United States Patent
Nandu et al.

(10) Patent No.: US 6,298,713 B1
(45) Date of Patent: Oct. 9, 2001

(54) METHOD FOR DETERMINATION OF WATER TRANSPORT IN BIOCOMPATIBLE MATERIALS

(75) Inventors: Mahendra P. Nandu; Eric J. Leibenguth, both of Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 09/568,290

(22) Filed: May 10, 2000

(51) Int. Cl.[7] .................................................. G01N 13/04
(52) U.S. Cl. ............................................................ 73/64.47
(58) Field of Search .................................. 73/64.47, 1.01; 204/415

(56) References Cited

U.S. PATENT DOCUMENTS

| | | | |
|---|---|---|---|
| 5,156,041 | * 10/1992 | Schaper et al. | 73/38 |
| 5,211,055 | * 5/1993 | Steudle et al. | 73/64.47 |
| 5,612,222 | * 3/1997 | Gordon et al. | 73/64.47 |
| 5,776,999 | 7/1998 | Nicolson et al. | 682/496 |

* cited by examiner

Primary Examiner—Hezron Williams
Assistant Examiner—Michael Cygan
(74) Attorney, Agent, or Firm—Robert B. Furr, Jr.; Denis A. Polyn

(57) ABSTRACT

A method is provided for determining the water diffusion coefficient of a biocompatible material. The method measures water diffusion through the biocompatible material by detecting the presence of hydrogen ions in $D_2O$ by NMR analysis.

5 Claims, 2 Drawing Sheets

METHOD FOR DETERMINATION OF WATER TRANSPORT IN BIOCOMPATIBLE MATERIALS

CROSS-REFERENCE to RELATED APPLICATIONS

This application is related to commonly-assigned applications U.S. Ser. Nos. 09/567931 and 09/567991 filed on even date herewith.

BACKGROUND

Water transport has been identified as a factor in the selection of biocompatible materials for medical applications, including ophthalmic lenses such as contact lenses. It would therefore be desirable to quantify in-vitro flux and diffusion coefficients of water, through biocompatible materials such as hydrogels.

U.S. Pat. No. 5,776,999 to Nicolson et al. discloses a method for screening materials for use as extended-wear ophthalmic lenses. The Nicolson et al. patent also discloses various methods for measuring the diffusivity of hydrogel materials.

Prior art methods for determining water transport require the preparation and use of buffered solutions. It would be desirable to provide a simpler laboratory technique that does not require the preparation and use of buffered solutions. It would also be desirable to provide a method that does not require the use of radio-labeled materials. Further, it would be desirable to provide a method that produces reliable results using readily available laboratory equipment.

SUMMARY OF THE INVENTION

The present invention provides a method for measuring the water diffusion coefficient across a sample of a water-permeable material, for example a biocompatible material such as hydrogel. The present invention provides a method for determining the water diffusion coefficient of a hydrogel material comprising the steps of:

(a) defining a calibration algorithm to relate the NMR spectra of at least three known concentrations of water in solution with $D_2O$, wherein the concentration of $D_2O$ is greater than the concentration of water;

(b) providing a first cell containing a first aqueous solution;

(c) providing a second cell containing a second solution comprising $D_2O$;

(d) equilibrating a sample of said biocompatible material in $D_2O$ and positioning said equilibrated sample of said biocompatible material at an interface between said first cell and said second cell to permit diffusion across said equilibrated sample of said biocompatible material;

(e) withdrawing a sample of said second solution;

(f) measuring the NMR spectrum of said withdrawn sample of said second solution;

(g) calculating the concentration of hydrogen ions in said second cell by applying the calibration algorithm of step (a) to said NMR spectrum of said second solution; and (h) calculating the water diffusion coefficient of said biocompatible material using the hydrogen ion concentration calculated in step (g).

The method of the invention may further comprise replacing a volume of solution in the second cell that is substantially equal to the volume of the withdrawn sample. In a preferred embodiment, the solution used to replace the withdrawn volume is substantially pure $D_2O$.

DETAILED DESCRIPTION

The invention provides a method for determining water transport through biocompatible materials, for example hydrogels and especially hydrogels useful as contact lens materials. As indicated above, while the present invention can be used in connection with a variety of biocompatible materials, it is especially useful with contact lens materials, the soft contact lens materials in particular, for example, hydrophilic lenses made from polymers having repeat units derived from hydrophilic monomers such as hydroxyethyl methacrylate, polyvinylpyrrolidone, dimethylacrylamide, methacrylic acid, or the like. These include hydrogels belonging to Groups I to IV (FDA categories). Group IV is distinguished from Groups I to III by having higher water content and is distinguished from Group I and II by being more ionic. Typically, Group IV lenses have a water content greater than 50% by weight. High water content is associated with materials having high oxygen permeability, resulting in the increasing popularity of Group IV lenses, especially disposable and frequent-replacement lenses. Such materials include, but are not limited to, bufilcon A, etafilcon A, methafilcon A, ocufilcon C, perfilcon A, phemfilcon A, and vifilcon A. Materials containing methacrylic acid monomers include methafilcon B, ocufilcon D, methafilcon A, and etafilcon A (USAN and the USAP Dictionary of Drug Names). Lenses made from the foregoing materials are commercially available from a variety of sources. Such lenses include daily-wear lenses, extended-wear lenses, planned-replacement lenses, and disposable lenses.

The flux of water through hydrogel membranes was determined by the equation $$J = m/t\,A \qquad (1)$$

where J=Flux in mg/hr cm$^2$ m=mg of water permeated through sample

A=Available area in cm$^2$ t=Time in hours

Knowing the flux J, the diffusion coefficient D, was calculated using Ficks first law of diffusion.

$$D = J\,\Delta x/\Delta c$$

where D=Diffusion coefficient in cm$^2$/hr.

$\Delta x$=Membrane thickness in cm $\Delta c$=Concentration gradient across the membrane in mg/cm$^3$ For the determination of water flux through the biocompatible material, a Varian model EM 360A-1171 NMR spectrometer (commercially available from Varian, Inc., 3120 Hansen Way, Palo Alto, Calif. 94304) was used to measure the increase in the hydrogen ion concentration of the receptor compartment.

Figure 1:
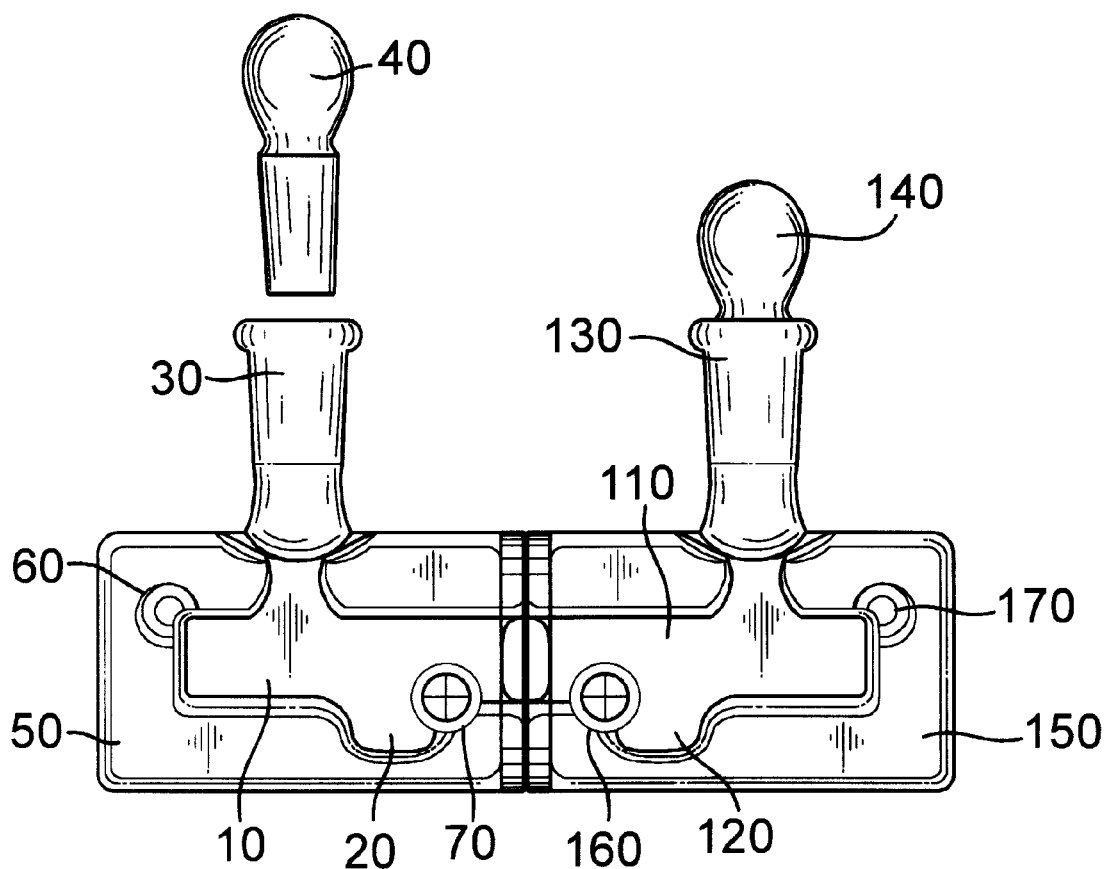
FIG. 1 is a simplified diagram of a diffusion cell apparatus useful in the present invention.

FIG. 1 illustrates a simplified diagram of a preferred diffusion cell apparatus useful in accordance with the present invention. Donor cell 10 and receiver cell 110 are mirror images of each other. Donor cell 10 includes stirring well 20 and port 30, which is equipped with removable stopper 40. Stirring well 20 contains a magnetic stirrer (not shown). Donor cell 10 is surrounded by heat transfer jacket 50, which includes heat transfer fluid inlet line 60 and heat transfer fluid outlet line 70. A ground glass flange (not shown) of donor cell 10 fits against a matching ground glass flange (not shown) of receiver cell 110. The ground glass flanges may optionally be recessed to receive a material sample for diffusion testing. Alternatively, the ground glass flanges may be ground flat to hold the material sample between the opposing flat ground surfaces.

Receiver cell 110 includes stirring well 120 and port 130, which is equipped with removable stopper 140. Stirring well 120 contains a magnetic stirrer (not shown). Receptor cell 110 is surrounded by heat transfer jacket 150, which includes heat transfer fluid inlet line 160 and heat transfer fluid outlet line 170.

The following examples measure the amount of water in mg/ml permeating through hydrogel membranes into the receptor compartment containing $D_2O$. The following Example 1 shows the NMR technique developed and employed in accordance with the invention.

The present invention determines the rate of water flux (and hence the diffusion coefficient for water) by measuring the rate at which hydrogen ions flow from the donor cell into the receiver cell. The NMR spectrum of a sample drawn from the receiver cell shows, at time=0, no significant hydrogen ion peaks.

The calibration algorithm of the invention correlates actual water concentrations in $D_2O$ with the total peak height or area under the hydrogen ion peaks for NMR spectra produced by analyzing known mixtures of $D_2O$ and water. The relationship between the summation of NMR hydrogen ion peak heights or hydrogen ion peak areas and hydrogen ion concentration in the $D_2O$-containing receiver cell has advantageously been found to be relatively linear within the concentration ranges of general interest in the present invention.

Example 1

Figure 2:
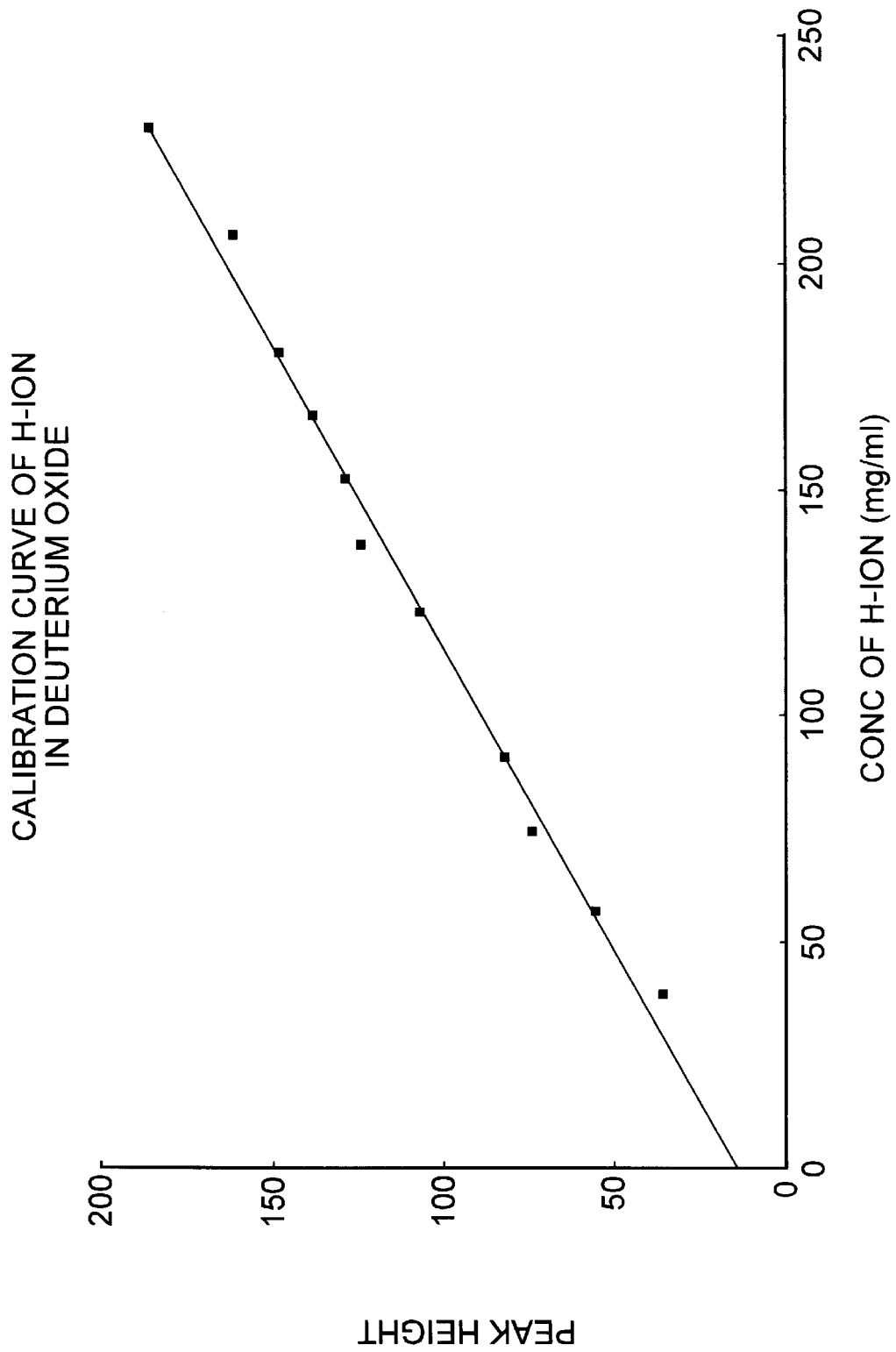
FIG. 2 shows a calibration curve of hydrogen ion peaks for H-ion concentrations in $D_2O$ in accordance with Example 1.

To 0.5 ml of $D_2O$ as a reference sample, known volumes of distilled water were added. The different peak heights for different H-ion concentrations in $D_2O$ were obtained as shown in FIG. 2. A calibration curve was obtained by plotting H-ion concentration in $D_2O$ (mg/ml) vs. peak height as shown in FIG. 2. All instrument parameters were kept constant during the entire operation which included developing a calibration curve and running the test sample. By knowing the peak height of the test sample, the concentration of the water in mg/ml in $D_2O$ could be determined from the calibration curve. Thus, the flux and the $DH_2O$ through hydrogels could be determined using the equations shown above.

Example 2

In the diffusion studies, hydrogel discs were held between two compartments of a stirred, jacketed diffusion cell. The diffusion cell is commercially available from Crown Glass Company, Inc. of Sommerville, N.J. (990 Evergreen Drive, Somerville, N.J. 08876). The solutions on both sides were stirred by stirrers to reduce boundary layer effects. The solutions were maintained at a temperature of 32±0.5° C. by circulating water through the jacket.

Example 2—Polymacon Hydrogel

The monomer mix was U.V. cured between two glass plates. The films of approximately 0.20 mm thickness were made. The films were boiled in distilled water for 5 hours at 80–85° C. to remove extractables and then equilibrated in distilled water. Circular sections of the equilibrated films were then cut, by using a 9 mm diameter core borer. The thicknesses of the discs were measured by a pneumatically controlled gauge.

For the measurement of $DH_2O$, the discs were equilibrated in $D_2O$. The $DH_2O$ was obtained by the NMR technique as mentioned earlier. Both the experiments were run with at least two discs of different thicknesses and the results are shown in Table 1.

TABLE 1

Diffusion Coefficients of Water Through Polymacon Hydrogel

| Thickness $\mu m$ | WATER $DH_2O \times 10^{-3}$ cm$^2$/hr |
|---|---|
| 245.5 ± 4.5 | 6.1 ± 0.5 |

Example 3—Lidofilcon Hydrogel

The monomer mix was heat cured between two glass plates. The films of three different thicknesses (thin, medium and thick) were made. The films were boiled in distilled water for 5 hours at 80–85° C. to remove extractables and then equilibrated in distilled water. The diffusion experiments on the cast discs and also through double-sided lathed discs were performed in a manner similar to polymacon discs. The results are tabulated in Table 2.

TABLE 2

Diffusion Coefficients of Water Through Lidofilcon Hydrogels

| Lidofilcon Hydrogel | Thickness $\mu m$ | WATER $DH_2O \times 10^{-2}$ cm$^2$/hr |
|---|---|---|
| Thin | 99.0 ± 5.0 | 2.0 ± 0.1 |
| Medium | 226.5 ± 13.5 | 2.6 |
| Thick | 887.0 | 2.9 ± 0.34 |
| Lathed | 253.7 ± 6.1 | 2.7 ± 0.1 |

Examples 4 and 5—HWS-1 and Etafilcon Hydrogels

HWS-1 and Etafilcon are high water content hydrogels sensitive to pH and ionic concentration of the medium in which they are bathed. The HWS-1 material contains 83.5 weight percent HEMA (hydroxy ethyl methacrylate), 10 weight percent IBOMA (isobornyl methacrylate), 0.5 weight percent BME (benzoin methyl ether) (catalyst), 6 weight percent MG (methacryloyl glycine) and 0.5 weight percent EDGMA (ethylene glycol dimethacrylate).

In buffered saline, HWS-1 and Etafilcon hydrate to 60 and 58% water content respectively. However, the water content of these hydrogels is 27.6 and 35.4% respectively in distilled water without previous exposure to the sodium ion. Also, HWS-1 resulted in 23% water content in 5% w/v saline solution. Thus, it is impractical to hydrate these ionic hydrogels in distilled water and run the diffusion experiments in a manner similar to non-ionic Polymacon and Lidofilcon hydrogels. The following approach was adopted to adjust the water content in these ionic hydrogels.

HWS-1 and Etafilcon discs were separately hydrated in known concentration of NaOH solution. pH of the solutions containing the hydrated discs was then adjusted to neutral by slow addition of HCl under stirring such that the resulting solutions had NaCl concentrations of 5% and 1% respectively. The water content of HWS-1 and Etafilcon discs were 60.33 and 57.8% respectively. The shifts in the concentration of NaCl from 5 to 4% for HWS-1 discs and 1 to 0.5% for Etafilcon discs resulted in only slight variation in hydration.

For the determination of $DH_2O$ in HWS-1, LHS cell compartment contained 3 ml of 5% NaCl in water and RHS cell compartment contained 3 ml of 4% NaCl in $D_2O$. The experiment was run for 15 minutes and a sample from RHS compartment was analyzed by NMR to determine $DH_2O$. A calibration curve of H-ion concentration in $D_2O$ was determined by taking 0.5 ml of 4% NaCl in $D_2O$ as a reference sample and then measuring the peak heights of the known concentration of water in the reference sample. A similar approach was followed in the determination of $DH_2O$ in Etafilcon discs. The results are summarized in Table 3.

TABLE 3

Diffusion Coefficients of Water Through HWS-1 and Etafilcon Hydrogels

| Hydrogel | WATER Thickness $\mu$m | $DH_2O \times 10^{-2}$ $cm^2/hr$ |
|---|---|---|
| HWS-1 | 193.3 ± 8.6 | 1.9 ± 0.25 |
| Etafilcon | 179.0 | 2.1 |

Examples 6 and 7

The objective is to match the water content of non-ionic hydrogel system, for e.g., Lidofilcon and the ionic hydrogel, for e.g., HWS-1 and then obtain the values for $DH_2O$ in these systems. Lidofilcon like films of different water contents were obtained by changing monomer compositions of N-vinylpyrollidone (NVP) and methylmethacrylate (MMA). Casting of the films and the determination of $DH_2O$ were followed in the usual manner as described earlier. The details of the different compositions and the diffusion coefficients are shown in Table 4.

TABLE 4

Diffusion Coefficients of Water Through Lidofilcon Type Non-Ionic Hydrogels

| Hydrogel | WATER Thickness $\mu$m | $DH_2O \times 10^{-2}$ $cm^2/hr$ |
|---|---|---|
| I | 243.5 | 2.5 ± 0.1 |
| II | 238.0 | 2.15 ± 0.05 |
| III | 238.0 | 1.6 ± 0.01 |
| IV | 231.0 ± 7.0 | 1.35 ± 0.15 |

RESULTS AND DISCUSSION

In Lidofilcon hydrogels, the values for $DH_2O$ (Table 2) are approximately 30x greater then the respective values for Polymacon (Table 1). The Lidofilcon double-sided lathed discs showed higher values of $DH_2O$ compared to the cast discs.

The cast Lidofilcon thin showed lower values for $DH_2O$ compared to Lidofilcon medium and thick.

Table 4 shows details on $DH_2O$ through Lidofilcon type non-ionic hydrogels. An increase in the composition of MMA from I to IV resulted in the leathery hydrogels with a decrease in the water content. As expected, the decrease in the water content of the hydrogels resulted in the lower values for $DH_2O$. Averaging the results of the formulations III and IV gave 60.79% hydration which is close to HWS-1 and values for $DH_2O$ as 0.015 $cm^2/hr$.

REFERENCES

1. L. Kline and T. DeLuca, An analysis of arcuate staining with the B&L Soflens—Part I, J. Am Optom. Assoc.; 46 (1975) 1126.
2. R. Miller, F. Brightbill and S. Slama, Superior limbic kerato-conjunctivitis in soft contact lens wearers, Cornea; 1 91982) 293.
3. D. Feurst, J. Sugar and S. Worobec; Superior limbic kerato-conjunctivitis associated with cosmetic soft contact lens wear, Arch. Ophthalmol; 101 (1983) 1214.
4. K. Zadinik and D. Mutti; Inferior arcuate corneal staining in soft contact lens wearers, Int. Contact Lens Clin.; 12 (1985) 110.
5. L. Kline, T. DeLuca and G. Fishberg; Corneal staining relating to contact lens wear, J. Am. Optom. Assoc.; 50 91979) 353.
6. B. Holden, D. Sweeney, A. Vannas, K. Nilsson and N. Efron; effect of long term extended contact lens wear on the human cornea, Invest. Ophthalmol. Vis. Sci.; 26 91985) 1489.
7. S. Zantos, G. Orsborn, H. Walter and H. Knoll; Studies on corneal staining with thin hydrogel contact lenses, Journal of the B.C.L.A., 9 (1986) 61.
8. W. Bachman and G. Wilson; Essential ions for maintenance of the corneal epithelial surface, Invest. Ophthalmol. Vis. Sci.; 26 91985) 1484.
9. S. Prabhakar and B. Misra; studies on the structural kinetic and thermodynamic parameters of cellulose acetate membranes, J. Membrane Sci.; 29 (1986) 143.

We claim:

1. A method for determining the water diffusion coefficient of a biocompatible material comprising the steps of:
   (a) defining a calibration algorithm to relate the NMR spectra of at least two known concentrations $H_2O$ in solution with $D_2O$, wherein the concentration of $D_2O$ is greater than the concentration of $H_2O$;
   (b) providing a first cell containing a first aqueous solution;
   (c) providing a second cell containing a second solution comprising $D_2O$;
   (d) equilibrating a sample of said biocompatible material in $D_2O$ and positioning said equilibrated sample of said biocompatible material at an interface between said first cell and said second cell to permit diffusion across said equilibrated sample of said biocompatible material;
   (e) withdrawing a sample of said second solution;
   (f) measuring the NMR spectrum of said sample of said second solution;
   (g) calculating the concentration of hydrogen ions in said second cell by applying the calibration algorithm of step (a) to said NMR spectrum of said second solution; and
   (h) calculating the water diffusion coefficient of said biocompatible material based upon the hydrogen ion concentration calculated in step (g).

2. The method of claim 1 further comprising replacing at least a portion of the liquid volume in said second cell after withdrawing said sample in step (e).

3. The method of claim 2 wherein said volume replacing step further comprises adding to said second cell a volume of substantially pure $D_2O$ substantially equal to the volume of the withdrawn sample.

4. The method of claim 1 wherein said biocompatible material is a hydrogel.

5. The method of claim 1 wherein said biocompatible material is a contact lens material.

* * * * *